(12) United States Patent
Mandavia et al.

(10) Patent No.: US 11,207,120 B2
(45) Date of Patent: Dec. 28, 2021

(54) EXTENDABLE ELECTROSURGICAL APPARATUS AND METHOD

(71) Applicant: Alfirin Technologies, LLC, Duluth, GA (US)

(72) Inventors: Dev Mandavia, Atlanta, GA (US); Devin Li, Painted Post, NY (US); Jack Corelli, Atlanta, GA (US); Samuel Hunter Hatcher, Atlanta, GA (US); Jason Weis, Gibsonia, PA (US)

(73) Assignee: Dev D. Mandavia, Duluth, GA (US)

( * ) Notice: Subject to any disclaimer, the term of this patent is extended or adjusted under 35 U.S.C. 154(b) by 448 days.

(21) Appl. No.: 15/913,289

(22) Filed: Mar. 6, 2018

(65) Prior Publication Data

US 2018/0250060 A1    Sep. 6, 2018

Related U.S. Application Data

(60) Provisional application No. 62/467,592, filed on Mar. 6, 2017.

(51) Int. Cl.
*A61B 18/08* (2006.01)
*A61B 18/00* (2006.01)

(52) U.S. Cl.
CPC .. *A61B 18/082* (2013.01); *A61B 2018/00589* (2013.01); *A61B 2018/00595* (2013.01); *A61B 2018/00601* (2013.01); *A61B 2018/00946* (2013.01); *A61B 2218/007* (2013.01); *A61B 2218/008* (2013.01)

(58) Field of Classification Search
CPC ............ A61B 18/082; A61B 2218/007; A61B 2018/00946; A61B 2018/00595; A61B 2218/008; A61B 2018/00589; A61B 2018/00601
USPC .......................................................... 606/29
See application file for complete search history.

(56) References Cited

U.S. PATENT DOCUMENTS

| | | | | |
|---|---|---|---|---|
| 3,234,356 A * | 2/1966 | Babb | ...................... | A61B 18/10 606/30 |
| 5,709,675 A * | 1/1998 | Williams | ............... | A61B 18/00 604/22 |
| 9,017,849 B2 * | 4/2015 | Stulen | ................. | H01M 2/1022 429/120 |
| 2004/0260280 A1 * | 12/2004 | Sartor | ............... | A61B 18/1482 606/37 |

(Continued)

*Primary Examiner* — Linda C Dvorak
*Assistant Examiner* — Nils A Potter
(74) *Attorney, Agent, or Firm* — Troutman Pepper Hamilton Sanders LLP; Ryan A. Schneider

(57) ABSTRACT

An electrosurgical device is described. The device can include a housing, a channel, and an actuator. The channel can comprise an electrode forming a tip. The actuator can be mechanically coupled to the electrode and the housing. The actuator can be configured to move between a first position and a second position and can be further configured to transition the tip from a retracted position when the actuator is at the first position to an extended position when the actuator is at the second position. A movement of the actuator from the first position to the second position can close an electrical circuit comprising the electrode and a source of electrical energy to generate a flow of current through the electrode for heating the tip to an elevated temperature suitable for cauterizing tissue.

10 Claims, 10 Drawing Sheets

(56) References Cited

U.S. PATENT DOCUMENTS

| | | | | |
|---|---|---|---|---|
| 2006/0217697 A1* | 9/2006 | Lau | A61B 18/085 | 606/29 |
| 2007/0049922 A1* | 3/2007 | Rontal | A61B 18/1402 | 606/41 |
| 2009/0062791 A1* | 3/2009 | Lee | A61B 18/1402 | 606/45 |
| 2011/0184404 A1* | 7/2011 | Walberg | A61B 18/1445 | 606/33 |
| 2011/0213356 A1* | 9/2011 | Wright | A61B 18/1477 | 606/33 |
| 2013/0178845 A1* | 7/2013 | Smith | A61B 18/1492 | 606/33 |
| 2014/0135757 A1* | 5/2014 | Bernard | A61B 18/1206 | 606/33 |
| 2015/0080876 A1* | 3/2015 | Worrell | A61B 18/1445 | 606/34 |
| 2019/0046259 A1* | 2/2019 | Batchelor | A61B 18/1233 | |

* cited by examiner

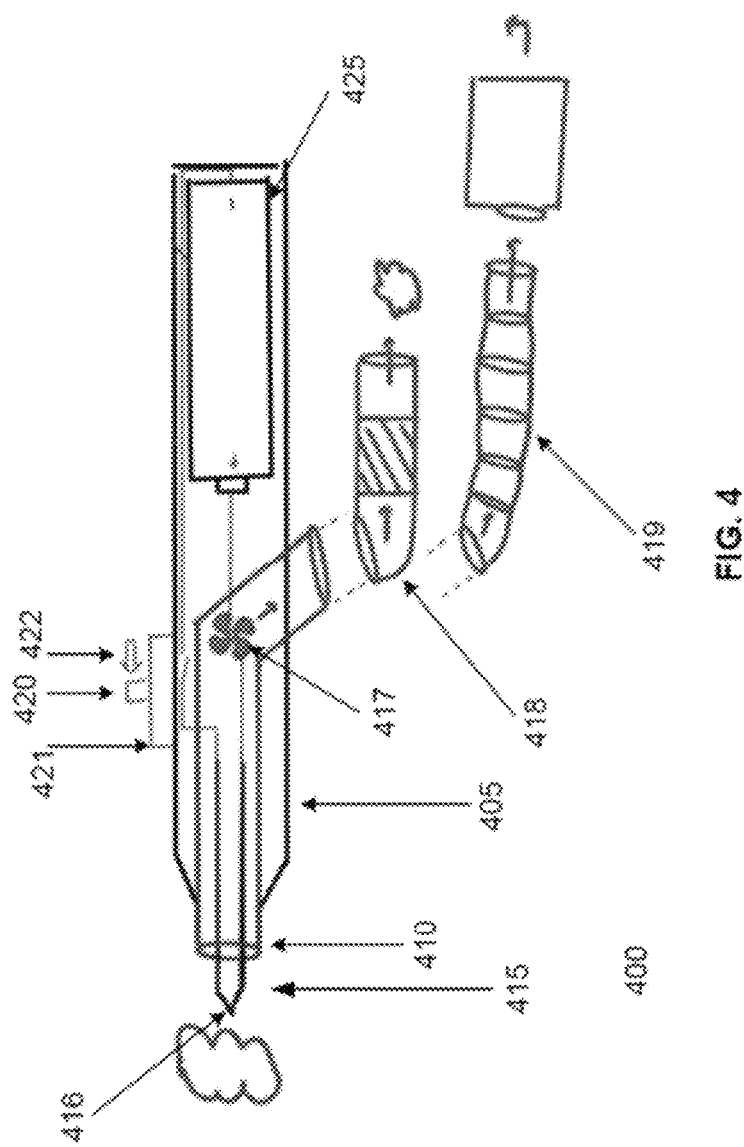

EXTENDABLE ELECTROSURGICAL APPARATUS AND METHOD

CROSS-REFERENCE TO RELATED APPLICATIONS

This application claims the benefit of U.S. Provisional Application Ser. No. 62/467,592, filed 6 Mar. 2017, which is incorporated herein by reference in its entirety as if fully set forth below.

TECHNICAL FIELD

The present invention relates generally to an electrosurgical device and corresponding method for using same. More specifically, the present invention relates to an electrocautery instrument having an extendable and retractable cauterizing tip that can be energized as it moves from its retracted position to its extended position and corresponding method for operating the instrument.

BACKGROUND

Surgical procedures involve incising, cutting, removing, fusing, and/or repairing body tissue (e.g., human or animal body). These functions can be performed using electrosurgical cutting instruments that use high frequency electrical energy to manipulate (e.g., cut or remove) tissue and/or coagulate bodily fluids (e.g., blood) during surgical procedures. Many surgeons use electrocautery instruments to perform surgical operations because such instruments tend to be safer, cleaner, and more efficient than other available alternatives.

SUMMARY

An extendable electrosurgical apparatus and corresponding method for using same is described.

In some embodiments, an electrosurgical device comprises a housing, a channel, and an actuator. The channel can comprise an electrode forming a tip. At least a portion of the channel can be contained within the housing. The actuator can be mechanically coupled to the electrode and the housing. The actuator can be configured to move between a first position and a second position. The actuator can be further configured to transition the tip from a retracted position when the actuator is at the first position to an extended position when the actuator is at the second position. A movement of the actuator from the first position to the second position can close an electrical circuit comprising the electrode and a source of electrical energy to generate a flow of current through the electrode for heating the tip to an elevated temperature suitable for cauterizing tissue.

In some embodiments, the actuator is a sliding actuator configured to slide along the body between the first and second positions.

In some embodiments, the actuator comprises a spring exerting force on the actuator in a first direction towards the first position.

In some embodiments, the actuator comprises opposing magnets generating a force on the actuator in a first direction towards the first position.

In some embodiments, the electrosurgical device further comprises a lock configured to hold the actuator in the second position.

In some embodiments, the channel comprises a fan configured to induce a flow of gas from an area proximate the tip of the electrode into the channel.

In some embodiments, the channel comprises an impeller configured to induce a flow of gas from an area proximate the tip of the electrode into the channel.

In some embodiments, the channel comprises a turbine configured to induce a flow of gas from an area proximate the tip of the electrode into the channel.

In some embodiments, the channel comprises a draft system with a negative suction mechanism using negative pressure to induce a flow of gas from an area proximate the tip of the electrode into the channel. As known to those skilled in the art, inducing a negative pressure and draft, may be accomplished by devices including, but not limited to, a fan, a turbine, an impeller, and the like.

In some embodiments, the electrosurgical device further comprises a filter configured to remove at least a portion of particulate matter in the gas after the gas enters the channel.

In some embodiments, the electrosurgical device further comprises an evacuation system configured to expel at least a portion of the gas after the gas enters the channel.

In some embodiments, a movement of the actuator from the first position to the second position activates the fan.

In some embodiments, a movement of the actuator from the first position to the second position activates the impeller.

In some embodiments, a movement of the actuator from the first position to the second position activates the turbine.

In some embodiments, a method of operating an electrosurgical device comprises applying a first force to an actuator of the electrosurgical device, which causes the actuator to transition from a first position at which a tip of an electrode of the electrosurgical device is at a retracted position to a second position at which the tip is at an extended position. Applying the first force to the actuator can close an electrical circuit comprising the electrode and a source of electrical energy and generate a flow of electrical current through the electrode for heating the tip to an elevated temperature suitable for cauterizing tissue.

In some embodiments, the electrosurgical device comprises a spring exerting a second force on the actuator in a direction towards the first position. The first force can be in a direction towards the second position. The first force can be greater than the second force.

In some embodiments, the electrosurgical device comprises opposing magnets generating a second force on the actuator in a direction towards the first position. The first force can be in a direction towards the second position. The first force can be greater than the second force.

In some embodiments, the method further comprises inducing a flow of gas from a location proximate the tip to an area within the electrosurgical device.

In some embodiments, the method further comprises filtering the gas after it enters the area within the electrosurgical device.

In some embodiments, the method further comprises expelling the gas from the electrosurgical device.

In some embodiments, applying the first force to the actuator closes an electrical circuit comprising a fan and the source of electrical energy, which activates the fan. In some embodiments, activation of the fan induces the flow of gas from the location proximate the tip to the area within the electrosurgical device.

In some embodiments, applying the first force to the actuator closes an electrical circuit comprising an impeller and the source of electrical energy, which activates the impeller. In some embodiments, activation of the impeller induces the flow of gas from the location proximate the tip to the area within the electrosurgical device.

In some embodiments, applying the first force to the actuator closes an electrical circuit comprising a fan and the source of electrical energy, which activates the turbine. In some embodiments, activation of the turbine induces the flow of gas from the location proximate the tip to the area within the electrosurgical device.

In some embodiments, an electrosurgical device comprises a housing, an electrode, a fan, and an actuator. The electrode can be positioned within the housing and can comprise a tip. The fan can be positioned within the housing. The actuator can be mechanically coupled to the electrode and the housing and can be configured to move between a first position and a second position. The actuator can be further configured to transition the tip from a retracted position when the actuator is at the first position to an extended position when the actuator is at the second position. A movement of the actuator from the first position to the second position can close an electrical circuit comprising the electrode, the fan, and a source of electrical energy to generate a flow of current through the electrode and fan. The flow of current can heat the tip to an elevated temperature suitable for cauterizing tissue. The flow of current can also activate the fan to induce a flow of gas from an area proximate the tip to an area within the housing.

In some embodiments, the electrosurgical device can further comprise a filter configured to filter a least a portion the gas after the gas enters the housing.

In some embodiments, the electrosurgical device can further comprise an evacuation system configured to expel at least a portion of the gas after the gas enters the housing.

In some embodiments, the actuator can be a sliding actuator configured to slide along the body between the first and second positions.

In some embodiments, the actuator comprises a spring exerting force on the actuator in a first direction towards the first position.

In some embodiments, the actuator comprises opposing magnets generating force on the actuator in a first direction towards the first position.

In some embodiments, the electrosurgical device can comprise a lock configured to hold the actuator in the second position.

In some embodiments, an electrosurgical device comprising an electrode and a sliding mechanism is disclosed. The electrode extends between two electrode ends and forms a tip for cauterizing tissue when heated. The sliding mechanism is mechanically coupled to the electrode and moves the tip from a retracted position to an extended position. A movement of the sliding mechanism to transition the electrode tip from the retracted position to the extended position closes an electrical circuit comprising the electrode and a source of electrical energy, such as a battery, and generates a flow of current through the electrode for heating the electrode tip to an elevated temperature suitable for cauterizing the tissue.

In some embodiments, a cauterization device is disclosed. The cauterization device comprises an electrically conductive electrode, which extends between two ends and has a tip configured for applying heat to a target area, first and second conductive rods, a sliding mechanism, and an electrically conductive element. The first and second conductive rods extend from a proximal end to a distal end. Each of the rods is electrically coupled at the proximal end thereof to one end of the conductive electrode. The first rod is electrically coupled at the distal end thereof to one terminal of a battery. The sliding mechanism is mechanically coupled to the rods for moving the conductive tip between a retracted position and an extended position. The electrically conductive element is electrically coupled at one end to the other terminal of the battery and at another end to the sliding mechanism such that a portion of the conductive element is in proximity of a portion of the second rod and separated therefrom when the tip is in the retracted position. The movement of the sliding mechanism to transition the conductive tip from the retracted position to the extended position causes contact between the portions of the conductive element and the second rod, thereby forming a closed electrical circuit between the tip and the battery that generates a flow of current through the tip for heating thereof to a temperature suitable for cauterizing tissue.

In some embodiments, a method for operating an electrosurgical device is disclosed. The method includes activating a sliding mechanism that transitions a tip of an electrode of the electrosurgical device from a retracted position to an extended position. The activation of the sliding mechanism causes closing of an electrical circuit comprising the electrode and a power supply and generates a flow of current through the electrode for heating the thereof to an elevated temperature suitable for cauterizing tissue, e.g., an elevated temperature in a range of about 400° C. to about 1300° C., and preferably in a range of about 750° C. to about 1300° C. The heated electrode can be used to cauterize the tissue.

In other examples, any of the aspects above, or any system, method, apparatus described herein can include one or more of the following features.

The electrosurgical device can include first and second electrically conductive rods that can be mechanically coupled to the sliding mechanism. Each of the rods can extend from a proximal end to a distal end and can be coupled at the proximal end to one electrode end. The first rod can be electrically coupled at the distal end thereof to a first terminal of the electrical energy source.

The electrosurgical device can include an electrically conductive element that can be electrically coupled at a distal end thereof to a second terminal of the energy source and at proximal end to the sliding mechanism such that a proximal portion of the conductive element can be in proximity of a distal portion of the second rod and separated therefrom when the electrode tip is in the retracted position, thereby forming an electrical open circuit between the electrode tip and the energy source. The movement of the sliding mechanism to transition the conductive tip from the retracted position to the extended position can cause at least partial contact between the proximal portion of the conductive element and the distal portion of the second rod so as to form a closed electrical circuit between the electrode tip and the energy source and generate a flow of current through the electrode for heating the electrode tip to a temperature suitable for cauterizing tissue.

In some embodiments, the electrosurgical device can include a thumb stud configured for moving the sliding mechanism. The thumb stud can be used to press on the proximal portion of the conductive element as the sliding mechanism moves the tip from the retracted position to the extended position so as to cause the at least partial contact between said distal portion of the second rod and the proximal portion of the electrically conductive element.

The energy source can be a battery. The sliding mechanism can include a thumb stud that can be configured for activating the sliding mechanism. In particular, the thumb stud can be used to move the sliding mechanism so as to transition the electrode from a retracted position to an extended position. In some embodiments, the electrosurgical device can include a spring that is coupled to the sliding mechanism and can bias the electrode when in the extended position. The spring can bring the electrode back to the retracted position when the sliding mechanism is deactivated. In some embodiments, the electrosurgical device can include opposing magnets coupled to the sliding mechanism and can bias the electrode when in the extended position.

The electrosurgical device and/or the cauterization device can comprise a shell for housing the device.

In another aspect, an electrosurgical device is disclosed, which includes an electrode extending between two ends and forming a tip for cauterizing tissue when heated; a sliding mechanism mechanically coupled to said electrode for moving said tip from a retracted position to an extended position, a plurality of conductive rods each of which is electrically coupled at a proximal end to one end of the electrode, said rods being mechanically coupled to said sliding mechanism, and a switch electrically coupled to said rods, said switch being in an open state when the electrode is in a retracted position, wherein a movement of the sliding mechanism to move the electrode from the retracted position to the extended position causes the switch to transition to a closed state, thereby allowing a flow of current through the electrode for heating thereof. A switch may comprise many different switches known in the art. For example, a switch may comprise a micro-switch.

Other aspects and advantages of the invention can become apparent from the following drawings and description, all of which illustrate the principles of the invention, by way of example only.

BRIEF DESCRIPTION OF THE DRAWINGS

The various aspects of the invention described above may be better understood by referring to the following description taken in conjunction with the accompanying drawings. The drawings are not necessarily to scale, emphasis instead generally being placed upon illustrating the principles of the invention.

FIG. 2B is a perspective view of the electrosurgical device shown in FIG. 2A.

FIG. 4 is a perspective view of an electrosurgical device according to an embodiment of the invention.

DETAILED DESCRIPTION

An electrosurgical apparatus and corresponding method for using same is described. The term "electrosurgical device," as used herein, refers broadly to a device designed to coagulate bodily fluids (e.g., blood), seal blood vessels, or cut, incise, destroy, remove, fuse, and/or repair tissue. Such electrosurgical (or electrocautery) devices generally operate by applying energy (e.g., in the form of heat), which can be generated using an electric current flowing through a conductive element of the device adapted for application of heat for a target area. The amount of electric current applied to the conductive element can depend on the type of application in which the device is being used. For example, a different energy level can be used for cutting tissue for sealing blood vessels or causing coagulation of bodily fluids.

The present invention generally provides an electrosurgical device that includes a retractable electrode adapted for applying heat energy to a target area, e.g., tissue and/or blood. The electrode can be moved from a retracted position, where it is fully enclosed by a housing of the device, to an extended position, where at least a portion of the electrode extends outside the housing and is exposed to the external environment. As the electrode is moved from the retracted position to the extended position, a closed electric circuit is established between the electrode and an energy source (e.g., a battery) so as to cause the flow of a current through the electrode, thereby raising the electrode's temperature.

Figure 1A:
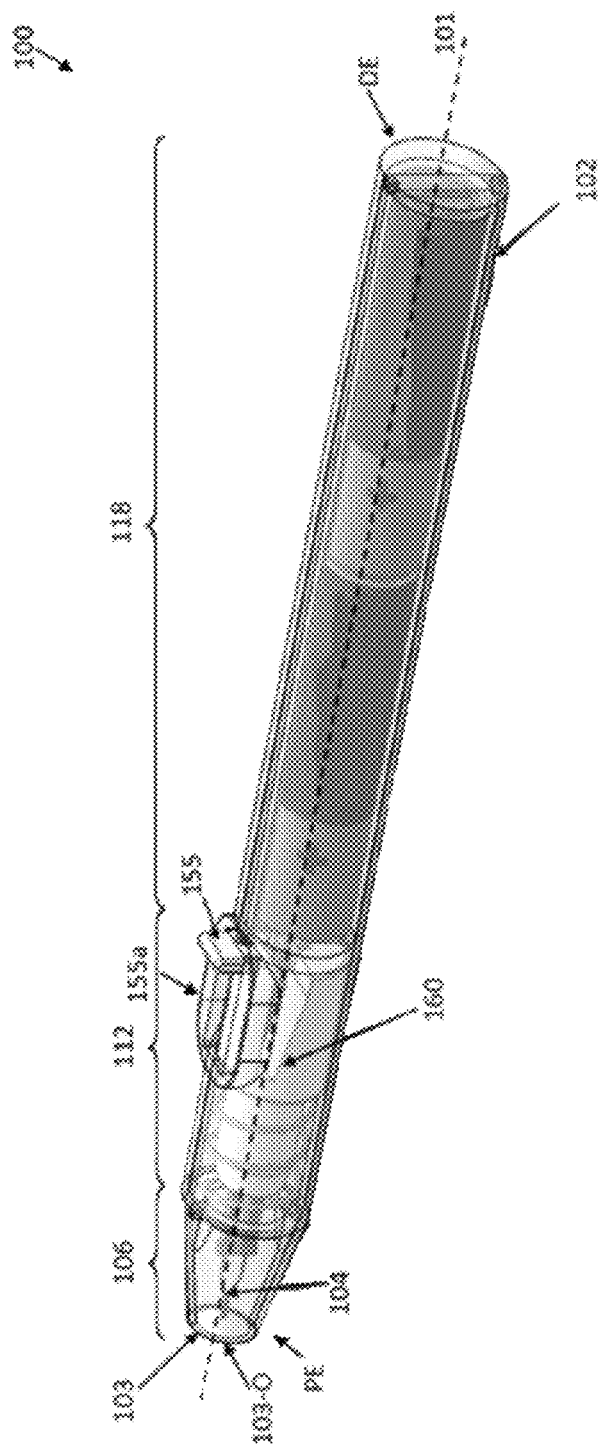
FIG. 1A is a perspective view of an electrosurgical device according to an embodiment of the invention.

FIG. 1A is a perspective view of an electrosurgical device 100 according to an embodiment, which includes a housing 102 having a tapered end 103. The housing 102 can be made from any suitable rigid or non-rigid material and assume any shape or configuration known or available in the art. By way of example, in some embodiments, the housing can be formed of a suitable plastic material, such as ABS (acrylonitrile butadiene styrene), PLA (polylactic acid) and PETG (polyethylene terephthalate). In the embodiment shown in FIG. 1A, the housing 102 is shown as having a generally cylindrical shape, extending from a proximal end (PE) to a distal end (DE). One skilled in the art should, however, appreciate that the embodiments described herein are not limited to housings that assume elongated or cylindrical shapes. For example, the housing can be box-shaped. Further, it should be noted that the term "distal," as used herein, refers to a portion of an element of the electrosurgical device 100 that is further from the end 103 and/or the body part upon which the device is being applied. Similarly, the term "proximal," as used herein, refers to a portion of an element that is closer to the end 103 and/or the body part upon which the device is being applied.

The housing 102 can comprise or be surrounded/coated by a non-conductive or an electrically insulating material. For example, the housing 102 can comprise an ultraviolet (UV) hardened printed resin and/or injection or extrusion molded ABS plastic. In one embodiment, the housing can comprise a ceramic material. Additionally or alternatively, the housing 102 can include sterilizable materials and/or material known to have antimicrobial properties.

Further, the housing 102 can be configured such that it can easily and/or comfortably fit into an operator's hand (not shown, e.g., a surgeon or a physician). For example, the housing 102 can be an elongated cylindrical housing having a longitudinal axis 101 that extends from the PE to the DE. The housing 102 can also include one or more features that prevent slippage or movement of the device 100 in the operator's hand. For example, the housing 102 can include any slip-resistant features known in the art. Alternatively, or additionally, the housing 102 can be made from a slip-resistant material.

The housing 102 can be described as having a number of compartments. For example, in the embodiment shown in FIG. 1A, the housing 102 is shown as having a proximal compartment 106, a central compartment 112, and a distal compartment 118. The features and components included within in each compartment are described in further detail below. In some embodiments, at least a segment of the housing portion forming a compartment can be removable, for example, to allow access to the interior of the compartment.

Figure 1B:
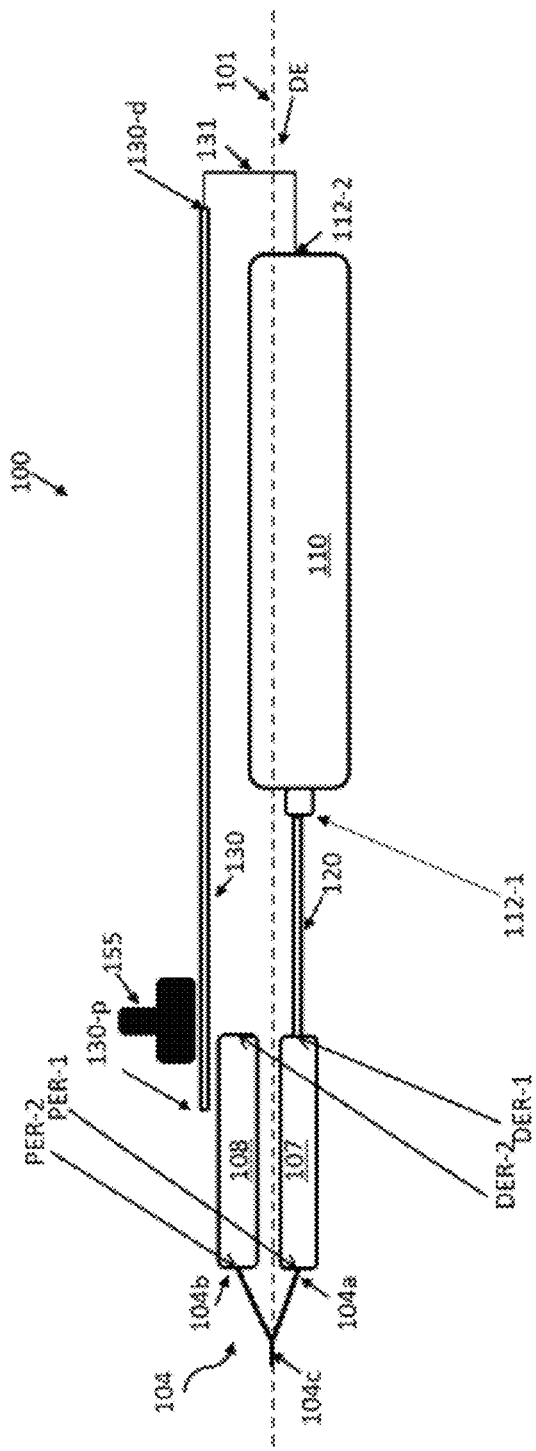
FIG. 1B is a high-level schematic illustration of an electrosurgical device according to the embodiments disclosed herein.

The proximal compartment 106 can shield the electrode 104 from the external environment when the electrode is in a retracted position (see, e.g., FIG. 1B). The compartment 106 terminates in the end 103 having an opening 103-O through which the electrode 104, or at least a portion thereof, can extend outside of the compartment 106 when the electrode is in an extended position.

The device 100 can also include an actuator, which is shown in the figures as a sliding mechanism 160 having a thumb stud 155, which can be used to activate the sliding mechanism 160. The invention, however, is not limited to sliding mechanisms, but rather can employ many types of actuators known in the art. In particular, a user can employ the thumb stud to move the sliding mechanism forward toward the end 103. In this embodiment, the thumb stud can travel along a slot 155a formed in the housing 102. Upon activation, the sliding mechanism 160, causes the electrode 104 (or at least some a part of thereof, such as electrode tip 104c) to move within the body 102 towards the opening 103-O and extend through the opening 103-O to the external environment. Once in the extended position, the electrode 104 can be used for electrosurgical applications, e.g., blood coagulation. As discussed in more detail below, the transition of the electrode 104 from the retracted position to the extended position results in establishing a closed electric circuit between the electrode and an energy source (e.g., a battery), thereby allowing the flow of a current through the electrode for heating thereof.

The electrosurgical device 100 can also include one or more spring elements 177, 178 coupled to the sliding mechanism 160, which can be used to bias the electrode 104 while the electrode is in the extended configuration. Further, the springs elements 177, 178 can help retract the electrode 104 through the opening 103-O into the housing 102 when the thumb stud 155 is released.

Figure 1C:
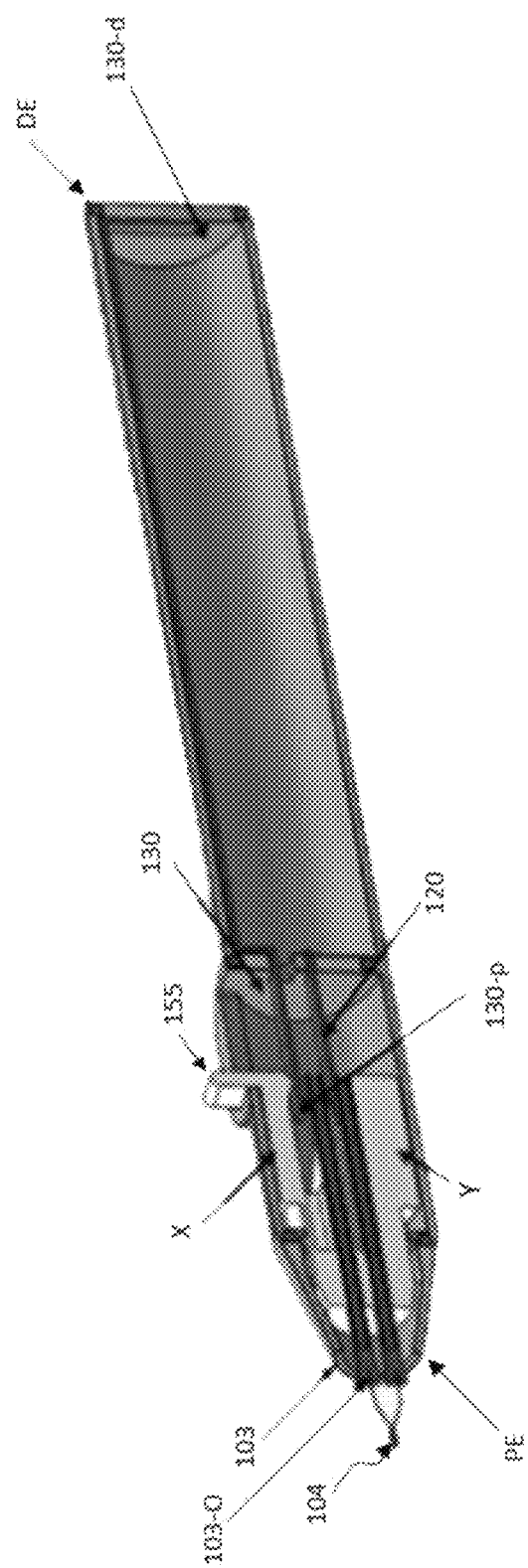
FIG. 1C is a cross-sectional view of an electrosurgical device according to an embodiment of the invention.

FIG. 1B is a high-level schematic illustration of some of the components that can be included in the housing 102 of the electrosurgical device 100 shown in FIG. 1A. FIG. 1C also includes a cross-sectional illustration of the exemplary electrosurgical device 100.

As noted with reference to FIG. 1A, the electrosurgical device 100 includes an electrically conductive electrode 104 disposed in the proximal compartment 106 (shown in FIG. 1A) of the housing 102. The electrode 104 can extend between two ends 104a and 104b and include a tip 104c configured for incising or cauterizing tissue (not shown). The electrode 104 can be any type of electrode 104 known, available, or used in the relevant art. Generally, the electrode 104 can be formed from any electrically conductive material known in the art. For example, the electrode 104 can be a silver-based material or comprise silver, which, in addition to its conductive properties, is known to have certain antimicrobial properties. Other examples of suitable materials include, but are not limited to Nichrome, aluminum alloy. Some other examples of suitable materials for forming the electrode include, without limitation, titanium, stainless steel, iron chromium aluminum, pure nickel, and chromium nickel carbon. In some embodiments, the electrode 104 can be formed of an alloy that can be rapidly heated to an elevated temperature. The term "rapidly," as used herein, refers to any time frame deemed suitable for the application at hand, considering that the device 100 can be used for surgical operations to incise and cauterize tissue and/or coagulate bodily fluids. The electrode 104 can be reusable or disposable.

Generally, the electrode 104 can be any electrode available in the art. For example, the electrode 104 can be a ball or an angled-ball electrode (generally used for fulguration or desiccation), a blade electrode (generally used for coagulation with the flat part of the blade or for cutting with the edge of the blade), a needle electrode (for use in making precise cuts and coagulations), or a round loop electrode (for dissecting tissue and obtaining tissue samples). One of ordinary skill in the art should, however, appreciate that the embodiments disclosed herein are not limited to such electrodes. Any electrode known and available in the art can be used with the embodiments disclosed herein.

As discussed above, the electrode 104 can be configured such that it is movable within the body 102 of the electrocautery device 100. Specifically, the electrode 104 can be retractable and arranged such that it remains shielded within the body 102 of the device 100 while the device 100 is not in use. Keeping the electrode 104 shielded within the body 102 can prevent accidental or unwanted damage to the surrounding tissue. Further, the electrode 104 can be coupled with features, such as those discussed above, that, upon being engaged, move the electrode 104 (or at least the electrode tip 104c) out of the body 102 and allow the electrode to come in contact with the tissue. Once disengaged or retracted, the electrode 104 can move back such that it is shielded by the body 102 and cannot have any undesired contact with the surrounding tissue.

In this embodiment, the electrosurgical device 100 can also include a pair of electrically conductive rods 107, 108 that extend along the longitudinal axis 101 of the device 100. Each of the electrically conductive rods 107, 108 can have a proximal end (PER-1, PER-2) and a distal end (DER-1, DER-2). The proximal ends PER-1, PER-2 of the electrically conductive rods 107, 108 are mechanically and electrically coupled to the two ends 104a, 104b of the electrode 104. Specifically, the proximal end PER-1 of the first electrically conductive rod 107 is mechanically and electrically coupled to the first end 104a of the electrode 104. Similarly, the proximal end PE2 of the second electrically conductive rod 108 is electrically and mechanically coupled to the second end 104b of the electrode 104.

The coupling of the two ends 104a, 104b of the electrode 104 to the distal ends DER-1, DER-2 of the electrically conductive rods 106 and 108 can be achieved in a variety of ways. Generally, any technique known in the art can be used to connect the electrically conductive rods 107, 108 to the ends of the electrode 104a, 104b so as provide an electrically conductive path therebetween. For example, the ends 104a, 104b of the electrode 104 can be clamped, welded, or otherwise secured to the proximal ends PER-1, PER-2 of the rods 107, 108 so as to provide an electrical connection between the electrode and the rods.

The electrically conductive rods 107, 108 can comprise any electrically conductive element known in the art. For example, the electrically conductive rods 107, 108 can comprise brass, copper, gold, silver, aluminum, or any other conductive element known in the art. Alternatively and/or additionally, the electrically conductive rods 107, 108 can comprise an alloy.

In this embodiment, the distal end DER-1 of the first electrically conductive rod 107 can be electrically and mechanically coupled to a first electrically conductive element 120. Generally, any technique known in the art can be used to mechanically and/or electrically couple the first electrically conductive rod 107 to the first electrically conductive element 120. For example, the electrically conductive rod 107 and the first electrically conductive element 120 can be coupled by welding, soldering, clamping, or otherwise directly connecting the units together without requiring any separate mechanical or electrical connecting or supporting elements.

The first electrically conductive element 120 can be any electrically conductive element known in the art. For example, the first electrically conductive element 120 can be a conductive wire (e.g., brass, copper, gold, silver, or aluminum wire), a conductive cable, a metallic foil (e.g., aluminum foil), a metallic or a conductive bar or rod, etc. The first electrically conductive element 120 can assume any suitable shape. For example, the first electrically conductive element 120 can be an elongated conductive element 120 that extends along the longitudinal axis of the body 102 of the electrosurgical device 100. The first electrically conductive element 120 can, at least in some part, be coated or surrounded by one or more layers of an insulating material. Any insulating material known in the art can be used to insulate the first electrically conductive element 120.

The first electrically conductive material 120 can further be mechanically and electrically connected at its distal end to an electrical power supply 110 (not shown in FIG. 1C), to a terminal of a battery. The power supply 110 can be any suitable power supply known in the art. For example, in the embodiments shown in FIGS. 1A-1B, the power supply 110 is shown as a conventional cylindrical dry battery (two batteries coupled in series in FIG. 1A), having a positive terminal 112-1 and a negative terminal 112-2. Alternatively or additionally, the power supply 110 can be a lithium ion battery.

Further, the power source 110 can be rechargeable, reusable, and/or disposable. Additionally or alternatively, the power source 110 can be a deferred action power source that allows for activation of the power source 110 and electrosurgical device 100 at the time of use, thereby preventing the power source 110 from draining itself prior to being used. Any deferred action battery known in the art can be used.

Although shown as having a single power supply 110 in FIG. 1A, one skilled in the art should appreciate that any number of power supplies 110 can be used. For example, as shown in FIG. 1A, two or more power supplies can be connected in series to one another to form the power supply 110 described herein.

Further, although shown as an internal power supply 110, the power supply 110 can be internal and/or external to the electrosurgical device 100 and can be connected to the first electrically conductive element 120 using any technique known in the art. For example, in the embodiment shown in FIG. 1B, the power supply 110 is included in the distal compartment 118 of the body 102 of the electrosurgical device. The distal compartment 118 can include one or more features that allow for removal and/or replacement of the power supply 110. For example, the distal compartment 118 can be configured such that it can be opened to allow access to the power supply 110. If an external power supply is used, the distal compartment can include one or more features that allow for connecting the first electrically conductive element 120 to the power source 110. For example, the distal compartment can include an electrical port (not shown) that can be used to connect the first electrically conductive element 120 to the external power source 110.

The electrosurgical device 100 can further include a second electrically conductive element 130 that also connects to the power supply 110, e.g., to another terminal of a battery. The second electrically conductive element 130 can include a proximal end 130-*p* and a distal end 130-*d*. In the example shown in FIG. 1B, the second electrically conductive element 130 connects to the power supply on its distal end 130-D. However, one skilled in the art should appreciate that any non-insulated part of the second electrically conductive element 130 can be connected to the power supply 110. The second electrically conductive element 130 can connect to the power supply 110 using any suitable technique known in the art (e.g., soldering, welding, or clamping the second electrically conductive element 130 to the power supply). For example, in the embodiment shown in FIG. 1B, the second electrically conductive element 130 is connected to the power supply 110 using a separate conductive element 131 (e.g., wire). In the example shown in FIG. 1C, the second conductive element 130 is configured such that it is fixed in place and can directly connect to the power supply 110 at its distal end 130-*d*.

One skilled in the art should appreciate that, although described as rods and shown as cylindrical/rectangular shaped objects, the electrically conductive rods 107, 108 and the electrically conductive elements 120, 130 can assume any shape known in the art without departing from the spirit and the scope of the disclosure.

The first and second conductive elements 120, 130 both attach to the sliding mechanism 160. The second conductive element 130 can be configured such that it attaches to the power supply 110 in one end (distal end 130-*d*) and connects to the sliding mechanism 160 at the other end (proximal end 130-*p*). Further, the second conductive element 130 can be configured such that it is in the proximity of the second conductive rod 108 but remains separated from the rod 108, thereby forming an electrical open circuit between the electrode tip 104 and the energy/power source 110.

Figure 1D:
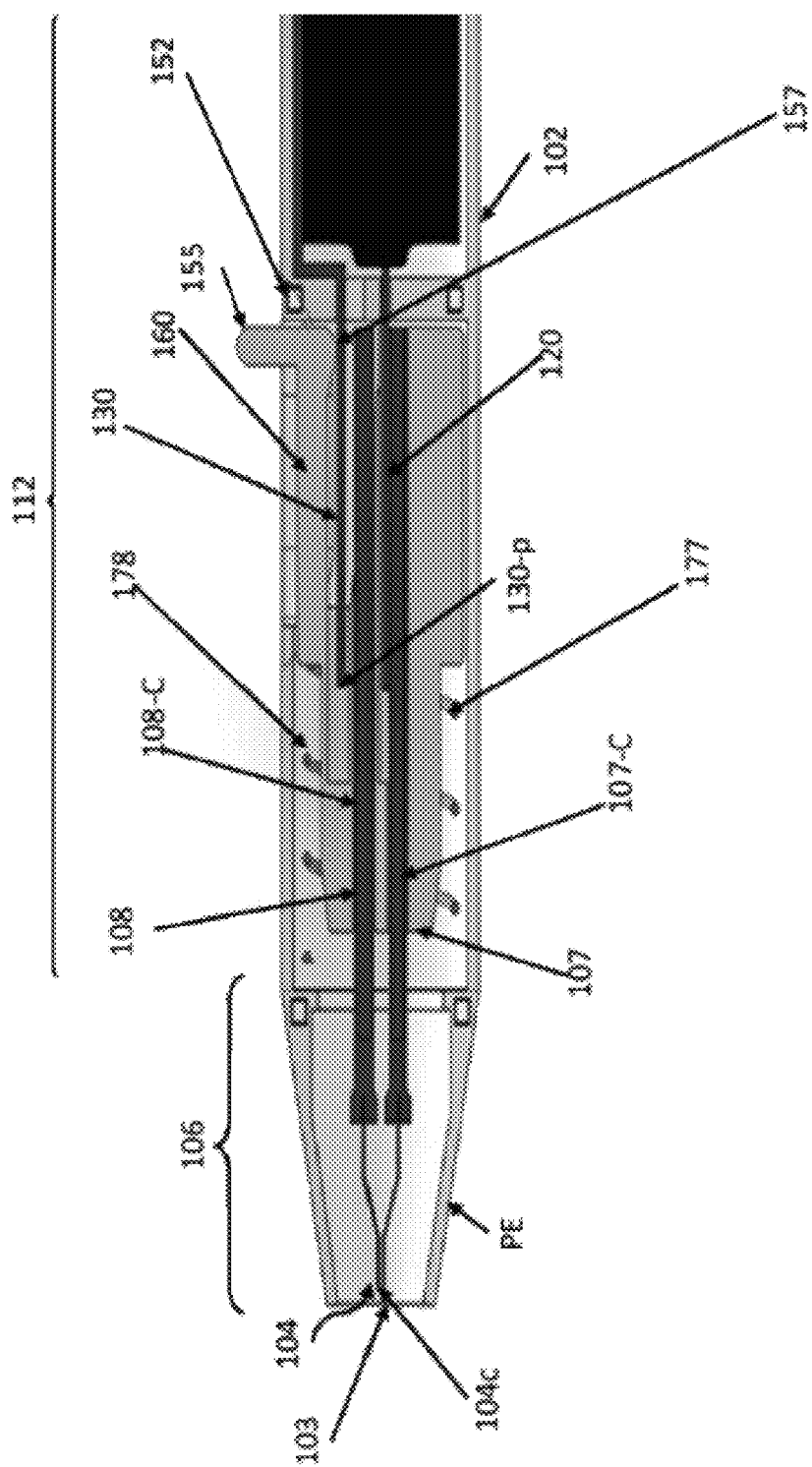
FIG. 1D is a cross-sectional illustration of a portion of the electrosurgical device shown in FIG. 1C.

FIG. 1D is a cross-sectional illustration of a portion of an example electrosurgical device 100, according to the embodiments described herein, that shows some of the features that can be included in the sliding mechanism 160.

As shown in FIG. 1D, the sliding mechanism 160 includes channels 107-C and 108-C that receive, respectively, a portion of the rods 107 and 108. For example, the rods 107 and 108 can be mechanically coupled to the sliding mechanism 160 such that the sliding mechanism 160 can be used to move the rods 107, 108 and the electrode 104 attached to the rods 107, 108 into and out of the tip 103 and the body 102. More specifically, as discussed in more detail below, the sliding mechanism 160 can be employed to move the electrode tip 104*c* between a retracted position, where the electrode tip 104*c* is within the housing, to an extended position, where the tip 104*c* extends beyond the housing 102 and is available for incising or cauterizing tissue.

The sliding mechanism 160 can be included in the central compartment 112 of the body 102. The sliding mechanism 160 can comprise any suitable material known in the art. For example, the sliding mechanism 160 can comprise a non-conductive material, a polymer, or any other material known in the art. Non-limiting examples of materials that can be used for the sliding mechanism 160 include injection molded ABS plastic or 3D printed ABS plastic.

As discussed above, the sliding mechanism 160 can include a thumb stud 155 that can be used to engage or release the sliding mechanism 160. Similar to the sliding mechanism 160, the thumb stud 155 can comprise any suitable material known in the art. Further, the thumb stud 155 and the sliding mechanism 160 can be two independent components that are coupled with one another using any suitable technique known in the art. Additionally or alternatively, the thumb stud 155 and the sliding mechanism 160 can be integral parts of the same structure.

The thumb stud 155 is generally used for releasable engagement of the sliding mechanism 160 by an operator. Specifically, the thumb stud 155 is configured such that it includes at least one portion that is exposed on the surface of the body 102 and/or protrudes out of the surface of the body 102. The portion of the thumb stud 155 that is exposed and/or protrudes out of the surface of the body 102 can be used by an operator to engage and/or release the sliding mechanism 160. The thumb stud 155 can assume any shape or configuration suitable for its intended use. Further, the thumb stud can be activated using any suitable technique known in the art and does not necessarily require application of a human "thumb" or finger for application.

In this embodiment, the thumb stud 155 includes a pointed bottom end 157 that is in contact with the second conductive element 130 and is configured to press on the conductive element 130 as the sliding mechanism is moved forward to transition the electrode 104 from the retracted position to the extended position. As the pointed end 157 of the thumb stud presses against the conductive element 130, it can bring a proximal portion of the conductive element 130 into contact with a distal portion of the second conductive rod 108. Once the second conductive element 130 is brought into contact with the second conductive rod 108, the combination of the first and second conductive rods 107, 108, the first and second conductive elements 120, 130, the electrode 104, and the power supply forms a closed electrical circuit, which results in the flow of a current through the electrode 104. In other words, as the sliding mechanism moves the electrode 104 from a retracted position to an extended position, a closed electric circuit is established between the electrode 104 and the power supply, which results in the flow of a current through the electrode 104 and heating thereof. In contrast, the release of the thumb stud can release the pressure on the conductive element 130 as the electrode 104 is retracted into the body 102, thereby interrupting the contact between the conductive element 130 and the conductive rod 108 and disconnecting the electrode 104 from the power supply. In other words, when the electrode 104 is in a retracted position, the proximal portion of the conductive element 130 is in proximity, but separated, from the distal end of the conductive rod 108. The movement of the sliding mechanism 160 brings the conductive element 130 into contact with the rod 108, thereby allowing the flow of current through the electrode 104.

Figure 1E:
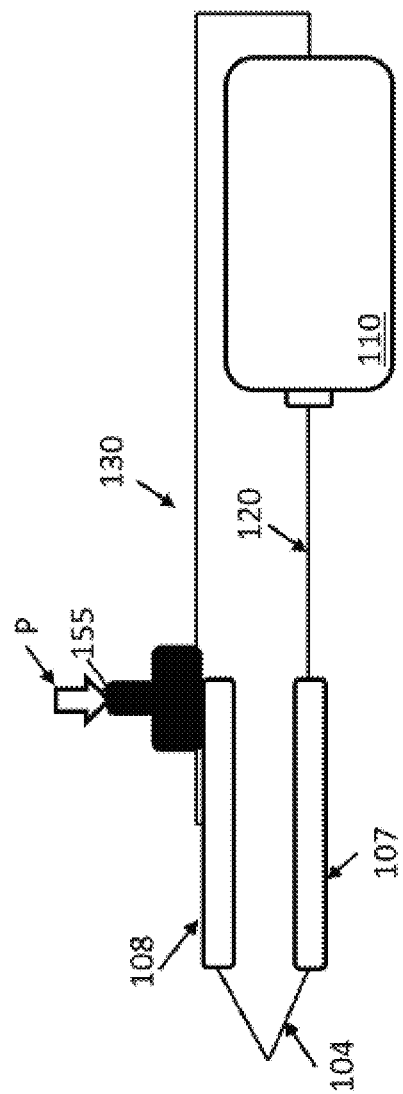
FIG. 1E is a high-level schematic illustration of an electric circuit that can be established in the electrosurgical device shown in FIG. 1A-FIG. 1D.

FIG. 1E is a high-level schematic illustration of a closed electric circuit that can be established in the electrosurgical device by activating the thumb stud 155. As shown in FIG. 1E, the movement of the thumb stud 155 and the pointed bottom portion 157 (not shown in FIG. 1D) can result in bringing the second conductive element 130 in contact with at least one portion of the second conductive rod 108. Once in contact with the second conductive rod 108, the combination of the first and second conductive rods 107, 108, the first and second conductive elements 120, 130, the electrode, and the power supply 110 forms a closed electrical circuit. The closed electrical circuit can provide the power necessary to heat the electrode 104 for use in incising or cauterizing tissue or coagulating bodily fluids.

Referring back to FIG. 1D, the first and second electrically conductive rods 107, 108 are connected to the sliding mechanism 160. The sliding mechanism 160 and the conductive rods 107, 108 can be connected using any technique known in the art. For example, as noted above, the sliding mechanism 160 can include one or more channels 107-C, 108-C that receive and secure at least a portion of the electrically conductive rods 107, 108.

As noted, the sliding mechanism 160 can be used to extend and retract the electrode tip 104. The sliding mechanism 160 is moveable within the body 102 and can move in response to the activation of the thumb stud 155. Specifically, once activated, the thumb stud 155 can cause the sliding mechanism 160 to move within the body 102. Any technique known in the art for moving the sliding mechanism can be used. For example, the thumb stud 155 can be used a slide the sliding mechanism 160 forward, towards the proximal end 103. Since the first and second conductive rods 107, 108 are connected to the sliding mechanism 160 through their corresponding channels 107-C, 108-C, the movement of the sliding mechanism 160 causes the conductive rods 107, 108 to also move within the body 102 towards the proximal end 103, and back, away from the distal end 103. Given that the electrode 104 is connected to the conductive rods 107, 108, by moving the conductive rods 107, 108, the sliding mechanism effectively moves the electrode 104 towards the distal end 103, and back, away from the tip 103.

Figure 2A:
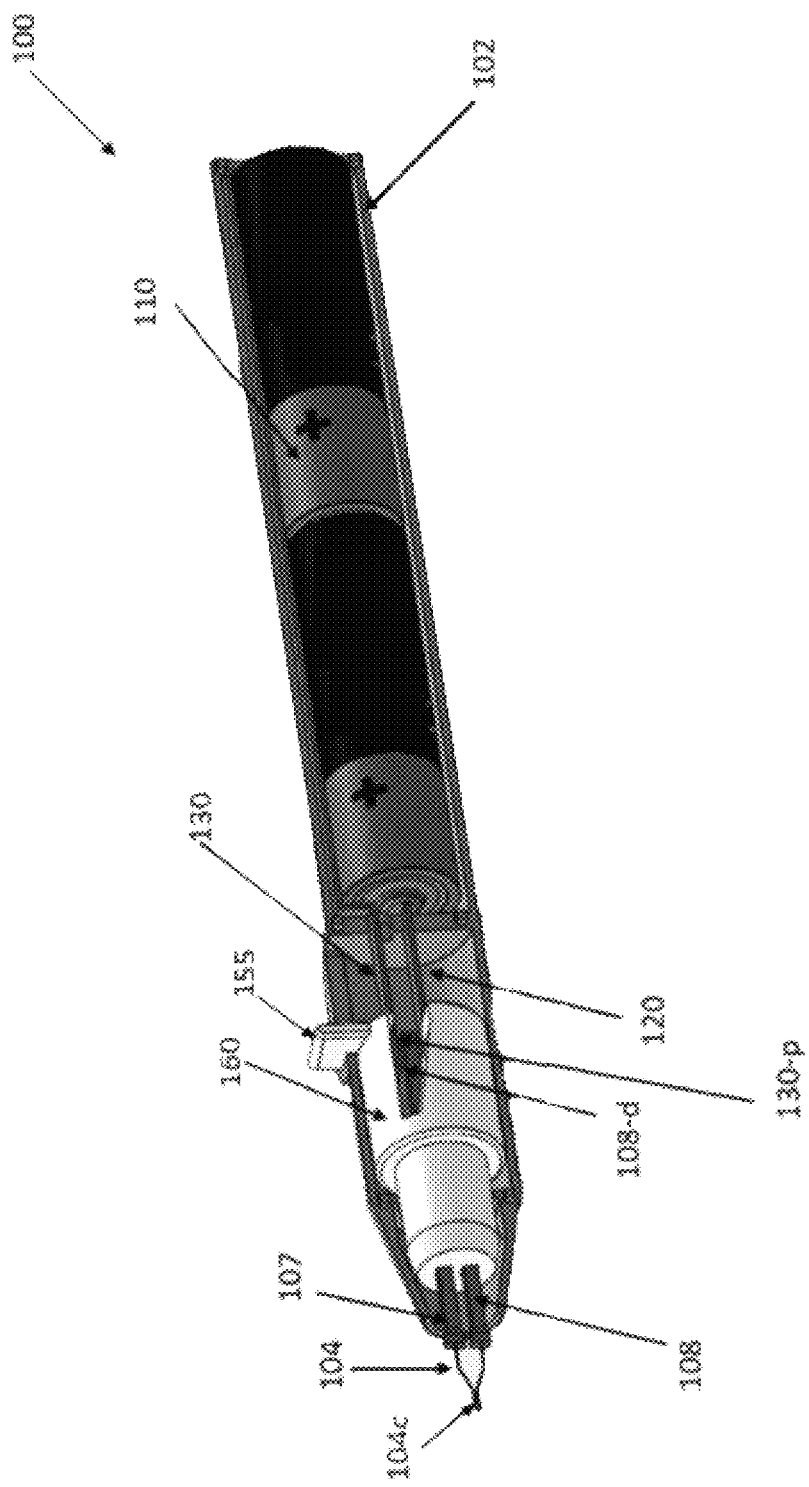
FIG. 2A is a side view of an electrosurgical device according to an embodiment of the invention.
Figure 28:
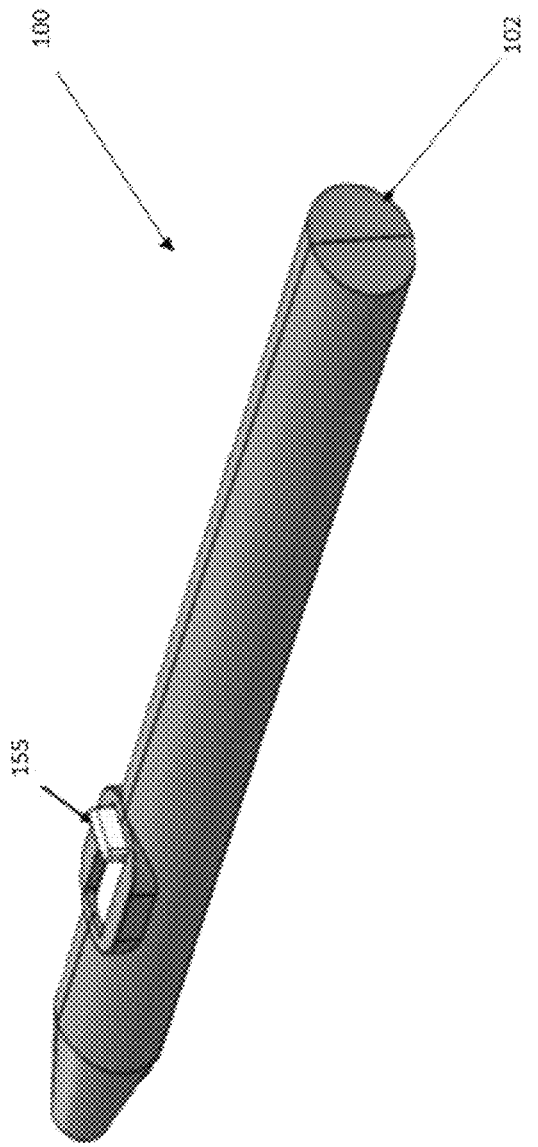

By way of further illustration, FIG. 2A is a side view of the electrosurgical device 100. In the drawing shown in FIG. 2A, one side of the housing 102 is not shown. As shown in FIG. 2A, while in the extended configuration, the electrode 104 (or at least the tip of the electrode 104c) is exposed for use in cauterizing, incising, or coagulating tissue and bodily fluids. Also, while in the extended configuration, the thumb slide 155 is moved forward to allow for sliding of the sliding mechanism 160 and the conductive rods 107, 108 that are coupled with the sliding mechanism. Further, as shown in FIG. 2A, the thumb slide 155, once engaged, brings at least one portion (e.g., the proximal portion 130-p) of the second conductive element 130 in contact with at least one portion (e.g., the distal portion 108-d) of the second conductive rod, thereby creating a closed electrical circuit. The electrical circuit includes the first and second conductive rods 107, 108, the first and second conductive elements 120, 130, the electrode, and the power supply 110. This electrical circuit provides the electrical power/energy needed to heat up the electrode 104 for use in incising, cauterizing, or coagulating tissue and bodily fluid.

FIG. 2B is a perspective view of the electrosurgical device 100 shown in FIG. 2A. FIG. 2B illustrates the device 100 in the retracted form. As shown, the electrode is completely shielded by the body 102 and is not visible. The thumb stud 155 remains visible and accessible in its retracted position.

Figure 3A:
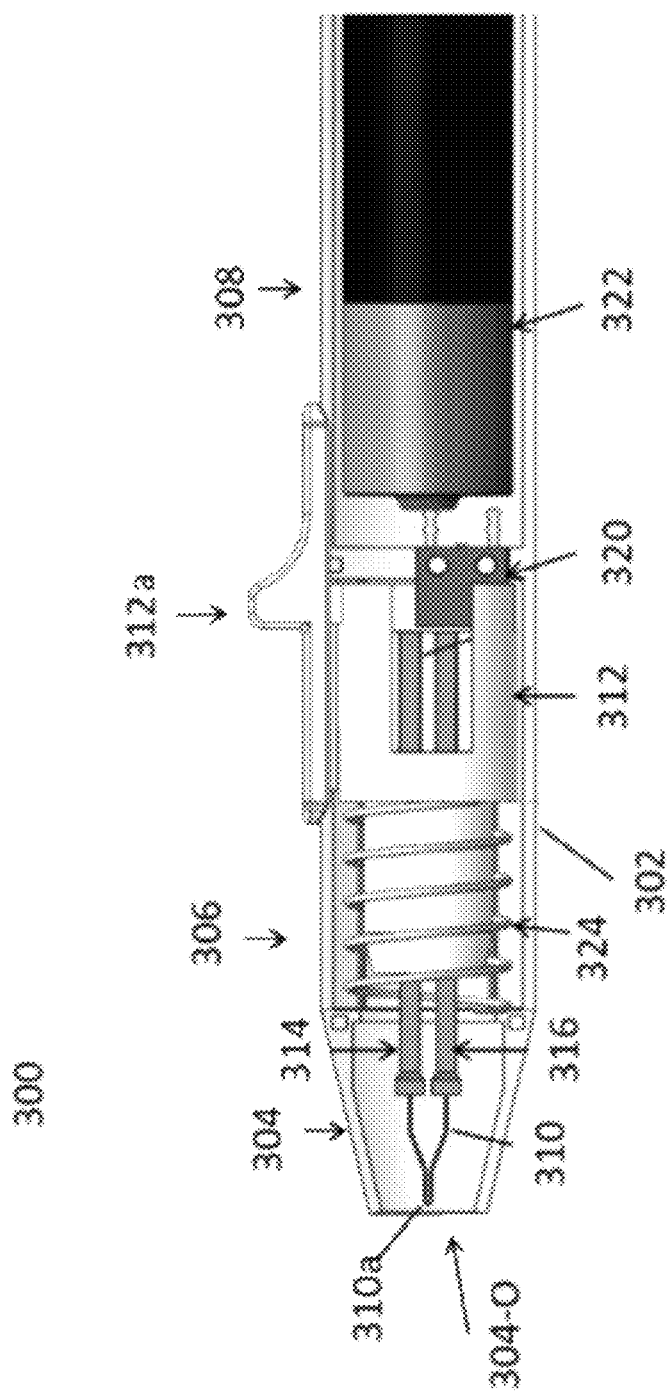
FIG. 3A is a schematic perspective view of another embodiment of an electrosurgical device according to the present teachings having a switch for closing an electric circuit between a cauterizing electrode and an energy source as the electrode is moved from a retracted position to an extended position (the switch shown in an open state in this figure).
Figure 3B:
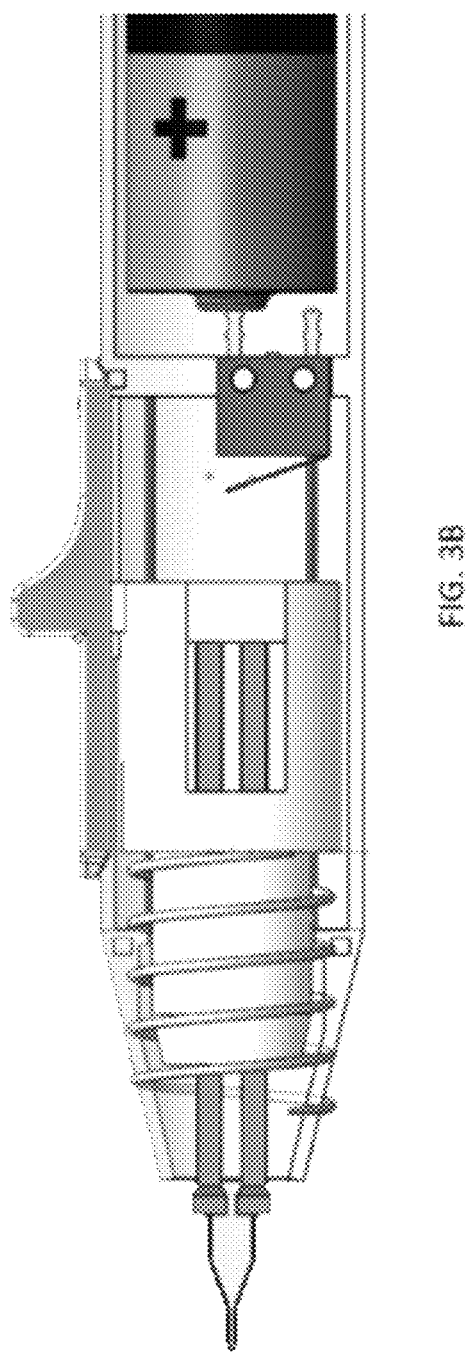
FIG. 3B is another schematic perspective view of the electrosurgical device of FIG. 3A where the switch is shown in a closed state.

FIGS. 3A and 3B schematically show another embodiment of an electrosurgical device 300 according to the present teachings. The electrosurgical device 300 is similar to the above electrosurgical device 100 discussed above except for the use of switch to close an electric circuit between an electrode and a battery as the electrode is moved between a retracted position and an extended position. More specifically, the electrosurgical device 300 includes a housing 302 includes a proximal compartment 304, a central compartment 306, and a distal compartment 308, where the proximal compartment 304 includes an opening 304-O. An electrode 310 is disposed in the proximal compartment and can be moved from a retracted position (depicted in FIG. 3A), in which the electrode is entirely enclosed by the proximal compartment 304, to an extended position (depicted in FIG. 3B), in which at least a tip 310a of the electrode protrudes through the opening 304-O to be exposed to the external environment.

With continued reference to FIGS. 3A and 3B, the electrosurgical device 300 includes a sliding mechanism 312 that is positioned entirely in the central compartment 306 when the electrode 310 is in the retracted position, and can be moved forward so as to enter partially into the proximal compartment 304, thereby moving the electrode 310 from the retracted position to the extended position, as discussed in more detail below. As discussed in more detail, the sliding mechanism 312 can be used to move the electrode 310 from the retracted position to the extended position.

The electrosurgical device 300 further includes two conductive rods 314 and 316, each of which is electrically coupled at a proximal end thereof to one end of the electrode 310. Each of the conductive rods 314 and 316 is coupled at its distal end to one terminal of a snap switch 320 disposed in the body 302. The switch 320 is coupled to a battery 322 disposed in the distal compartment 308 and can couple the conductive rods 314 and 316, and hence the electrode 310, to the battery when the electrode is in the extended position.

More specifically, the conductive rods 314 and 316 are mechanically coupled to the sliding mechanism 312 at their distal ends thereof. The sliding mechanism further includes a thumb stud 312a that can be used to move the sliding mechanism within the housing 302. Further, a spring 324 is coupled to the sliding mechanism 312.

In use, the thumb stud 312a can be used by an operator to move the sliding mechanism forward so as to move the electrode 310 from the retracted position to the extended position. The spring 324 biases the electrode in its extended position. The forward movement of the sliding mechanism causes the switch 320 to transition from an open state to a closed state, thereby establishing a closed electrical circuit between the battery and the electrode 310 via the conductive rods 314 and 316. This electrical connection between the battery and the electrode results in flow of a current to the electrode, thereby heating the electrode to an elevated temperature. Once the thumb stud is disengaged, the spring causes the sliding mechanism to move back, thereby moving the electrode from the extended position to the retracted position. As the electrode is moved to the retracted position, the switch is opened, via the sliding mechanism, thus stopping the flow of current to the electrode.

As shown in FIG. 4, in some embodiments, the electrosurgical device can comprise a fan 417, wherein the fan 417 is positioned within the housing 405. As known to those skilled in the art, many different devices induce a negative pressure and draft, including, but not limited to, a fan, a turbine, an impeller, and the like. Turning to the present drawing, the fan 417 is configured to induce a flow of gas from an area proximate the tip 416 of the electrode 415 into the channel 410. Accordingly, the fan permits a gas, such as smoke, created through the cauterization of tissue to be removed from the location proximate the cauterizing site. In some embodiments, the electrosurgical device can comprise an evacuation system 419, wherein the evacuation system 419 may be configured to expel at least a portion of the gas after the gas enters the channel 410. According to some embodiments, the evacuation system 419 may be positioned externally from the housing 405. In other embodiments, the evacuation system 417 may be positioned at least partially within the housing 405. Some embodiments may include a filter 418, wherein the filter 418 is configured to remove at least a portion of particulate matter in the gas after the gas enters the channel 410. According to some embodiments, the filter 418 may be positioned externally from the housing 405. In other embodiments, the filter 418 may be positioned at least partially within the housing 405. It should be noted that some embodiments may include both the evacuation system 417 and the filter 418.

The electrosurgical device 400 may further comprise an actuator 420 in some embodiments. The actuator 420 can be mechanically coupled to the electrode 415 and the housing 405. Some embodiments may include a sliding actuator, wherein the sliding actuator is configured to slide between a first and second position. In some embodiments, the actuator may comprise a spring 422 exerting force on the actuator 420 in a first direction towards the first position. The spring 422 may exert a second force on the actuator 420 in a direction towards the first position, wherein the first force is in a direction towards the second position, and wherein the first force is greater than the second force. The actuator may further comprise a lock 421 configured to hold the actuator 420 in the second position.

In some embodiments, the actuator 420 may be configured to move from a first position to a second position. Movement of the actuator 420 from the first position to the second position transitions the tip 416 from a retracted position to an extended position. Moving the actuator 420 from the first position to the second position closes an electrical circuit comprising the electrode 415 and a source of electrical energy 425 to generate a flow of current through the electrode 415 for heating the tip 416 to an elevated temperature suitable for cauterizing tissue. Additionally, the movement of the actuator 420 from the first position to the second position activates the fan 417, thereby inducing a flow of gas through the channel 410. As will be appreciated, the spring 422 requires application of persistent force in order for the electrode 415 and tip 416 to perform cauterization. As will be further appreciated, when the actuator 420 is in the second position, the fan 417 automatically runs during cauterization.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims. Further, the features illustrated or described in connection with one example embodiment may be combined with the features of other embodiments. Such modifications and variations are intended to be included within the scope of the present disclosure. Further, in the present disclosure, like-numbered components of the embodiments generally have similar features and/or purposes.

What is claimed is:

1. An electrosurgical device, comprising:
   a housing, comprising:
      a proximal compartment, containing a channel comprising an opening and an electrode forming a tip, the proximal compartment shielding the electrode in a retracted position, and the channel configured to allow the electrode to move between the retracted position and the opening such that the electrode is in an extended position protruding through the opening;

a central compartment connected to the proximal compartment, the central compartment containing:

an actuator mechanically coupled to the electrode, the actuator configured to move between a first position and a second position such that the actuator transitions the tip from the retracted position when the actuator is at the first position to the extended position when the actuator is at the second position;

a fan configured to induce a flow of gas through the channel from an area proximate the tip of the electrode into the channel;

a filter in fluid communication with the channel configured to filter the gas;

an evacuation system in fluid communication with the channel, the filter, and the fan, the evacuation system configured to receive the gas from the fan and the filter and expel the gas outside of the housing; and a slot on an exterior surface of the central compartment, the slot containing a thumb stud connected to the actuator, the thumb stud configured to engage the actuator to transition the actuator between the first and the second position; and a distal compartment connected to the central compartment opposite the proximal compartment, the distal compartment containing a power supply;

a first and a second conductive element connected to the power supply; and a first and a second conductive rod connected to the electrode, wherein the first conductive rod is connected to the first conductive element and the second conductive rod is in proximity to, but separated from, the second conductive element;

wherein a movement of the thumb stud causes the actuator to move from the first position to the second position, and the thumb stud presses on the second conductive element to contact the second conductive rod, such that an electrical circuit is formed comprising the electrode, the first and the second conductive rods, the first and the second conductive elements, and the power supply to:

generate a flow of current through the electrode for heating the tip to an elevated temperature suitable for cauterizing tissue; and activate the fan such that the flow of gas is created from the area proximate the tip of the electrode into the channel and out of the housing through the evacuation system.

2. The electrosurgical device of claim 1, wherein the actuator is a sliding actuator configured to slide along the central compartment between the first and second positions.

3. The electrosurgical device of claim 1, wherein the actuator comprises a spring exerting force on the actuator in a first direction towards the first position.

4. The electrosurgical device of claim 3, further comprising a lock configured to hold the actuator in the second position.

5. A method of operating an electrosurgical device, the method comprising:

applying a first force to an actuator of the electrosurgical device, which causes the actuator to contact a first conductive element connected to a power supply;

transitioning the actuator from a first position at which a tip of an electrode of the electrosurgical device is at a retracted position to a second position at which the tip is at an extended position;

contacting the first conductive element with a first conductive rod connected to the electrode, the electrode further connected to a second conductive rod, wherein the second conductive rod is connected to a second conductive element, and wherein the second conductive element is connected to the power supply; and expelling a gas generated from a location proximate the tip through an evacuation system to an area outside of the electrosurgical device;

wherein the contacting closes an electrical circuit comprising the electrode, the first and the second conductive elements, the first and the second conductive rods, and the power supply and generates a flow of electrical current through the electrode for heating the tip to an elevated temperature suitable for cauterizing tissue, and wherein the evacuation system comprises a fan in electrical communication with the power supply and a filter, the fan activating during the contacting such that the fan induces the flow of gas from the location proximate the tip, through the filter, to an area in the evacuation system within the electrosurgical device, and to the area outside of the electrosurgical device.

6. The method of claim 5, wherein the electrosurgical device comprises a spring exerting a second force on the actuator in a direction towards the first position, wherein the first force is in a direction towards the second position, and wherein the first force is greater than the second force.

7. An electrosurgical device, comprising:

a housing including a proximal compartment, a central compartment, and a distal compartment;

a channel within the housing, the channel comprising an opening in the proximal compartment;

an electrode positioned within the channel, the electrode being at least partially shielded by the proximal compartment in a retracted position and at least partially protruding through the opening in an extended position;

an actuator positioned within the central compartment, the actuator mechanically coupled to the electrode and the housing, the actuator configured to move between a first position and a second position, the actuator further configured to transition a tip of the electrode from the retracted position when the actuator is at the first position to the extended position when the actuator is at the second position;

a power supply contained in the distal compartment, the power supply connected to a first and a second conductive element;

a first and a second conductive rod connected to the electrode in proximity to, but separated from, the first and the second conductive elements; and an evacuation system configured to expel at least a portion of a gas after the gas enters the housing, the evacuation system comprising:

a fan configured to, when the electrode is at the extended position, induce a flow of the gas such that at least a portion of the channel is at a negative pressure with respect to an area proximate the tip of the electrode, which further induces a flow of the gas from the area proximate the tip of the electrode to an area within the channel, which further induces a flow of the gas from the area within the channel to an area outside of the housing; and a filter configured to filter at least a portion the gas after the gas enters the channel, wherein a movement of the actuator from the first position to the second position closes an electrical circuit between the first and the second conductive rods and the first and the second conductive elements to generate a flow of current from the power supply through the electrode, the flow of current heating the tip to an elevated temperature suitable for cauterizing tissue.

8. The electrosurgical device of claim 7, wherein the actuator is a sliding actuator configured to slide along the housing between the first and second positions.

9. The electrosurgical device of claim 7, wherein the actuator comprises a spring exerting force on the actuator in a first direction towards the first position.

10. The electrosurgical device of claim 7, further comprising a lock configured to hold the actuator in the second position.

\* \* \* \* \*